US009562960B2

(12) United States Patent
Kolipaka et al.

(10) Patent No.: US 9,562,960 B2
(45) Date of Patent: Feb. 7, 2017

(54) METHOD FOR MAGNETIC RESONANCE ELASTOGRAPHY INVERSION USING A FINITE MEDIUM MODEL

(75) Inventors: Arunark Kolipaka, Rochester, MN (US); Armando Manduca, Rochester, MN (US); Kiaran P. Mcgee, Rochester, MN (US); Richard L. Ehman, Rochester, MN (US); Kevin J. Glaser, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1346 days.

(21) Appl. No.: 12/935,968

(22) PCT Filed: Apr. 3, 2009

(86) PCT No.: PCT/US2009/039493
§ 371 (c)(1),
(2), (4) Date: Jan. 4, 2011

(87) PCT Pub. No.: WO2009/124263
PCT Pub. Date: Oct. 8, 2009

(65) Prior Publication Data
US 2011/0092798 A1    Apr. 21, 2011

Related U.S. Application Data

(60) Provisional application No. 61/042,437, filed on Apr. 4, 2008.

(51) Int. Cl.
*A61B 5/055*    (2006.01)
*G01R 33/563*    (2006.01)
*A61B 5/00*    (2006.01)

(52) U.S. Cl.
CPC ....... *G01R 33/56358* (2013.01); *A61B 5/0051* (2013.01); *A61B 5/416* (2013.01)

(58) Field of Classification Search
CPC .. A61B 5/416; A61B 5/0051; G01R 33/56358
(Continued)

(56) References Cited

U.S. PATENT DOCUMENTS 5,825,186 A    10/1998    Ehman et al.
7,257,244 B2 *    8/2007    Miga .............................. 382/128

OTHER PUBLICATIONS

The International Search Report and Written Opinion under date of Aug. 4, 2009 in connection with PCT/US09/039493.
(Continued)

*Primary Examiner* — Joseph M Santos Rodriguez
(74) *Attorney, Agent, or Firm* — Quarles & Brady LLP

(57) ABSTRACT

A method for magnetic resonance elastography ("MRE") is described, in which an MRE inversion that accounts for waves propagating in a finite, bounded media is employed. A vibratory motion is induced in a subject and MRE is performed to measure one or more components of the resulting displacement produced in the subject. This displacement data is subsequently filtered to provide a more accurate and computationally efficient method of inversion. Wave equations based on the geometry of the bounded media are then utilized to calculate the material properties of the subject. Such a method allows for the performance of MRE on tissues such as the heart, eye, bladder, and prostate with more accurate results.

11 Claims, 4 Drawing Sheets

(58) Field of Classification Search
USPC ......... 600/410, 411; 382/128, 131, 217, 218
See application file for complete search history.

(56) References Cited

OTHER PUBLICATIONS

Litwiller D.V. et al: "Mr Elastography of the Eye: Initial Feasibility" Proceedings of HTE Joint Annual Meeting ISMRM/ESMRMB, May 19, 2007 (May 19, 2007), p. 1262, XP002537969.

Houten Van E E W et al: "An Overlapping Subzone Technique for MR-Based Elastic Property Reconstruction" Magnetic Resonance in Medicine, Academid Press, Duluth, MN US, vol. 42, No. 4, Oct. 1, 1999; pp. 779-786; XP001182730; ISSN: 0740-3194.

Oliphant T.E. et al: "Complex-valued stiffness reconstruction for magnetic resonance elastography by algebraic inversion of the differential equation" Magnetic Resonance in Medicine Wiley USA, vol. 45, No. 2, Feb. 2001; pp. 299-310; XP-002537970; ISSN: 0740-3194.

Kolipaka A. et al: "Magnetic Resonance Elastography Based Method for Quantitating Shear Stiffness within a Heart Simulating Phantom Using a Thing Spherical Shell Model"; Proceedings of the International Society for Magnetic Resonance in Medicine, 16th Annual Meeting Proceedings, May 3, 2008; p. 1030; XP002537971.

Kolipaka A. et al: "Validation of MR Elastography Derived Stiffness Maps Using Established Pressure-Volume Model in a Simulated Heart Model"; Proceedings of the International Society for Magnetic Resonance in Medicine, 16thh Annual Meeting Proceedings, May 3, 2008; p. 1031; XP002537972.

Litwiller D.V. et al: "MRE of the Eye: Inversion using a thin Spherical-Shell Model"; Proceedings of the International Society for Magnetic Resonance in Medicine, 16th Annual Meeting Proceedings; May 3, 2008; p. 1550; XP002537973.

Chen Q et al: "Differential effects of pre-tension on shear wave propagation in elastic media with different boundary conditions as measured by magnetic resonance elastography and finite element modeling"; Journal of Biomechanics, Pergamon Press, New York, NY US; vol. 39, No. 8; Jan. 1, 2006; pp. 1428-1434; XP024980229; ISSN: 0021-9290.

Samani A. et al: "Constrained Non-linear Elasticity Reconstructon for Breast MRI Elastography" Proceedings of the ITN Ernational Society for Magnetic Resonance in Medicine, Eleventh Meeting Proceedgins, Jul. 10, 2003; XP002537974.

S Papazoglou et al: Horizontal Shear Wave Scattering From a Nonwelded Interface Observed by Magnetic Resonance Elastography; Physics in Medicine and Biology 52 (2007) 675-684.

Andreas Lienemann et al: Detection and Mapping of Intraabdominal Adhesions by Using Functional Cine MR Imaging: Preliminary Results; Radiology, Nov. 2000, vol. 217, No. 2; pp. 421-425.

Kevin J. Glaser et al: Shear Stiffness Estimation Using Intravoxel Phase Dispersion in Magnetic Resonance Elastography; Magnetic Resonance in Medicine 50:1256-1365 (2003).

M. Muthupillai et al: Magnetic Resonance Elastography by Direct Visualizaton of Propagating Acoustic Strain Waves; Science, vol. 269 20; Sep. 1995: http://www.jstor.org; Mon Mar. 10 12:03:59 2008.

M. Yin et al: Assessment of Hepatic Fibrosis With Magnetic Resonance Elastography; Clinical Gastroenterology and Hepatology 2007; vol. 5:1207-1213.

\* cited by examiner

METHOD FOR MAGNETIC RESONANCE ELASTOGRAPHY INVERSION USING A FINITE MEDIUM MODEL

CROSS-REFERENCE TO RELATED APPLICATIONS

This application claims the benefit of PCT International Application No. PCT/US2009/039493 filed on Apr. 3, 2009, which claims benefit of U.S. Provisional patent application Ser. No. 61/042,437 filed on Apr. 4, 2008 and entitled "System and Method for Magnetic Resonance Elastography", both of which are incorporated herein by reference.

STATEMENT REGARDING FEDERALLY SPONSORED RESEARCH

This invention was made with government support under EB001981 by the National Institute of Biomedical Imaging and Bioengineering. The government has certain rights in this invention.

BACKGROUND OF THE INVENTION

The field of the invention is magnetic resonance imaging ("MRI") methods and systems. More particularly, the invention relates to magnetic resonance elastography ("MRE") inversion methods and systems.

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well known reconstruction techniques.

It has been found that MR imaging can be enhanced when an oscillating stress is applied to the object being imaged in a method called MR elastography ("MRE"). The method uses the oscillating stress to produce shear waves that propagate through the organ, or tissues, to be imaged. These shear waves alter the phase of the MR signals, and from this the material properties of the subject can be determined. In many applications, the production of shear waves in the tissues is a matter of physically vibrating the surface of the subject with a device referred to as an "MRE driver." Shear waves may also be produced, for example, in the breast and prostate by direct contact with the oscillatory device. Also, with organs like the liver, the oscillatory force can be directly applied by means of an applicator that is inserted into the organ.

It has been suggested that cardiac dysfunction is related to the mechanical properties of the myocardium and that knowledge of these parameters could provide insight into a variety of diseases. Exemplary diseases include diastolic dysfunction, hypertension, and myocardial ischemia. To date, however, the application of MRE to quantify myocardial tissue mechanical properties has provided inaccurate results.

Like the heart and many organs in the body, disease states of the eye, such as macular degeneration, myopia, and cancer are also often indicated by changes in the mechanical properties of its constituent tissues. Assessments of ocular, intraocular, and orbital rigidity, however, are currently limited to qualitative assessment by direct palpation, more invasive methods, or other conventional methods such as tonometry. Yet, these methods may yield indirect or inaccurate results. As with the heart, to date, MRE has yet to be applied to determine the material properties of the eye in an accurate manner.

It would therefore be desirable to have a system and method for non-invasively analyzing the mechanical properties of organs such as the heart and eye.

SUMMARY OF THE INVENTION

The present invention overcomes the aforementioned drawbacks by providing a method for magnetic resonance elastography ("MRE") inversion that accounts for waves propagating in a finite, bounded media. A vibratory motion is induced in the subject and MRE is performed to measure one or more components of the resulting displacement vector distribution throughout the subject. The acquired data is subsequently filtered to provide a more accurate and computationally efficient method of inversion. Wave equations based on the geometry of the bounded media are used to construct a model that includes an equation or system of equations that is solved using the measured displacements to yield the material properties of the subject.

It is another aspect of the invention to provide a method for MRE inversion in a bounded medium. In the case where the bounded medium is more appropriately described in non-Cartesian coordinates, a coordinate system transformation is applied to measured displacement data to convert them from the Cartesian coordinate system in which they were measured to a coordinate system that better models the bounded medium under investigation. The MRE inversion method can be applied to finite media modeled as, for example, beams, plates, and shells.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
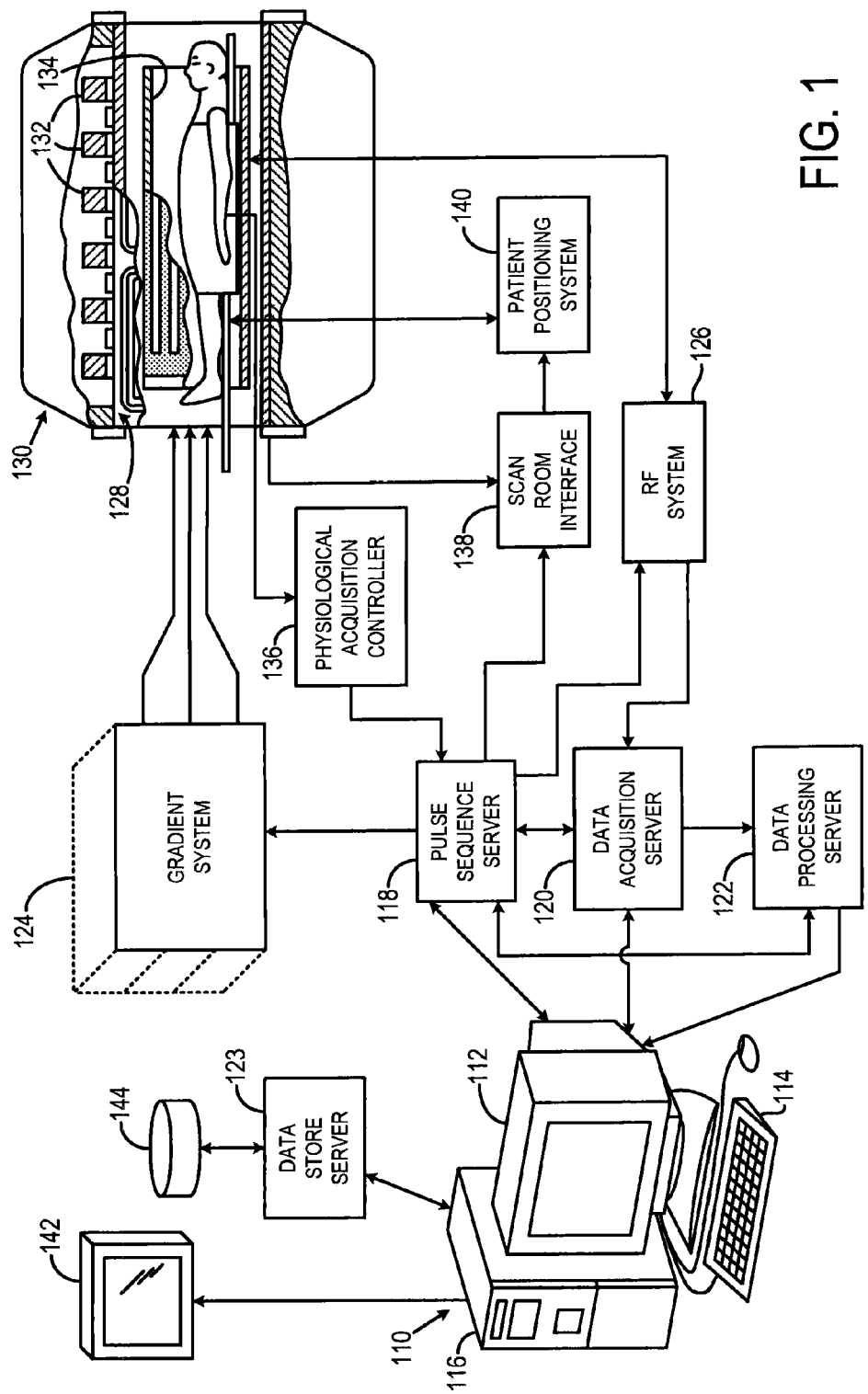
FIG. 1 is a block diagram of an MRI system that employs the present invention.

Referring particularly to FIG. 1, the preferred embodiment of the invention is employed in an MRI system. The MRI system includes a workstation 110 having a display 112 and a keyboard 114. The workstation 110 includes a processor 116 that is a commercially available programmable machine running a commercially available operating system. The workstation 110 provides the operator interface that enables scan prescriptions to be entered into the MRI system. The workstation 110 is coupled to four servers: a pulse sequence server 118; a data acquisition server 120; a data processing server 122, and a data store server 123. The workstation 110 and each server 118, 120, 122 and 123 are connected to communicate with each other.

The pulse sequence server 118 functions in response to instructions downloaded from the workstation 110 to operate a gradient system 124 and an RF system 126. Gradient waveforms necessary to perform the prescribed scan are produced and applied to the gradient system 124 that excites gradient coils in an assembly 128 to produce the magnetic field gradients $G_x$, $G_y$, and $G_z$ used for position encoding MR signals. The gradient coil assembly 128 forms part of a magnet assembly 130 that includes a polarizing magnet 132 and a whole-body RF coil 134.

RF excitation waveforms are applied to the RF coil 134 by the RF system 126 to perform the prescribed magnetic resonance pulse sequence. Responsive MR signals detected by the RF coil 134 or a separate local coil (not shown in FIG. 1) are received by the RF system 126, amplified, demodulated, filtered and digitized under direction of commands produced by the pulse sequence server 118. The RF system 126 includes an RF transmitter for producing a wide variety of RF pulses used in MR pulse sequences. The RF transmitter is responsive to the scan prescription and direction from the pulse sequence server 118 to produce RF pulses of the desired frequency, phase and pulse amplitude waveform. The generated RF pulses may be applied to the whole body RF coil 134 or to one or more local coils or coil arrays (not shown in FIG. 1).

The RF system 126 also includes one or more RF receiver channels. Each RF receiver channel includes an RF amplifier that amplifies the MR signal received by the coil to which it is connected and a detector that detects and digitizes the I and Q quadrature components of the received MR signal. The magnitude of the received MR signal may thus be determined at any sampled point by the square root of the sum of the squares of the I and Q components:

$$M=\sqrt{I^2+Q^2},$$

and the phase of the received MR signal may also be determined:

$$\phi = \tan^{-1}\left(\frac{Q}{I}\right).$$

The pulse sequence server 118 also optionally receives patient data from a physiological acquisition controller 136. The controller 136 receives signals from a number of different sensors connected to the patient, such as ECG signals from electrodes or respiratory signals from a bellows. Such signals are typically used by the pulse sequence server 118 to synchronize, or "gate", the performance of the scan with the subject's respiration or heart beat.

The pulse sequence server 118 also connects to a scan room interface circuit 138 that receives signals from various sensors associated with the condition of the patient and the magnet system. It is also through the scan room interface circuit 138 that a patient positioning system 140 receives commands to move the patient to desired positions during the scan.

The digitized MR signal samples produced by the RF system 126 are received by the data acquisition server 120. The data acquisition server 120 operates in response to instructions downloaded from the workstation 110 to receive the real-time MR data and provide buffer storage such that no data is lost by data overrun. In some scans the data acquisition server 120 does little more than pass the acquired MR data to the data processor server 122. However, in scans that require information derived from acquired MR data to control the further performance of the scan, the data acquisition server 120 is programmed to produce such information and convey it to the pulse sequence server 118. For example, during prescans MR data is acquired and used to calibrate the pulse sequence performed by the pulse sequence server 118. Also, navigator signals may be acquired during a scan and used to adjust RF or gradient system operating parameters or to control the view order in which k-space is sampled. And, the data acquisition server 120 may be employed to process MR signals used to detect the arrival of contrast agent in a magnetic resonance angiography (MRA) scan. In all these examples the data acquisition server 120 acquires MR data and processes it in real-time to produce information that is used to control the scan.

The data processing server 122 receives MR data from the data acquisition server 120 and processes it in accordance with instructions downloaded from the workstation 110. Such processing may include, for example: Fourier transformation of raw k-space MR data to produce two or three-dimensional images; the application of filters to a reconstructed image; the performance of a backprojection image reconstruction of acquired MR data; the calculation of functional MR images; the calculation of motion or flow images, etc.

Images reconstructed by the data processing server 122 are conveyed back to the workstation 110 where they are stored. Real-time images are stored in a data base memory cache (not shown) from which they may be output to operator display 112 or a display 142 that is located near the magnet assembly 130 for use by attending physicians. Batch mode images or selected real time images are stored in a host database on disc storage 144. When such images have been reconstructed and transferred to storage, the data processing server 122 notifies the data store server 123 on the workstation 110. The workstation 110 may be used by an operator to archive the images, produce films, or send the images via a network to other facilities.

Figure 2:
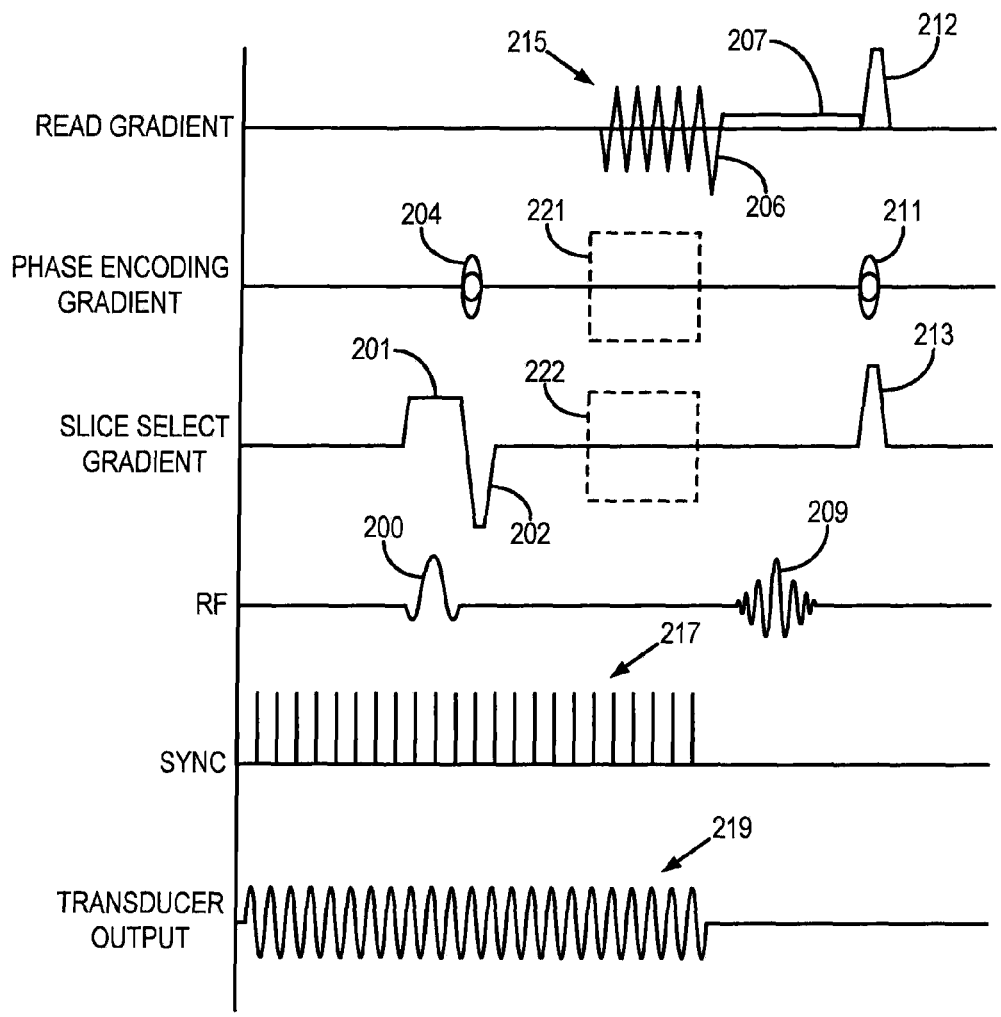
FIG. 2 is a graphic representation of an exemplary magnetic resonance elastography ("MRE") pulse sequence employed by the MRI system of FIG. 1.

Referring particularly to FIG. 2, an exemplary pulse sequence, which may be used to acquire magnetic resonance ("MR") data according to an embodiment of the present invention, is shown. The pulse sequence is fundamentally a 2DFT pulse sequence using a gradient recalled echo. Transverse magnetization is produced by a selective 90 degree radiofrequency ("RF") excitation pulse 200 that is produced in the presence of a slice select gradient, $G_z$, pulse 201 and followed by a rephasing gradient pulse 202. A phase encoding gradient, $G_y$, pulse 204 is then applied at an amplitude and polarity determined by the view number of the acquisition. A read gradient, $G_x$, is applied as a negative dephasing lobe 206, followed by a positive readout gradient pulse 207. An MR echo signal 209 is acquired 40 milliseconds after the RF excitation pulse 200 during the readout pulse 207 to frequency encode the 256 digitized samples. The pulse sequence is concluded with spoiler gradient pulses 212 and 213 along read and slice select axes, and a rephasing gradient pulse 211 is applied along the phase encoding axis ("$G_y$-axis"). As is well known in the art, this rephasing pulse 211 has the same size and shape, but opposite polarity of the phase encoding pulse 204. The pulse sequence is repeated 128 times with the phase encoding pulse 204 stepped through its successive values to acquire a 128-by-256 array of complex MR signal samples that comprise the data set.

An alternating magnetic field gradient is applied after the transverse magnetization is produced and before the MR signal is acquired. In the pulse sequence illustrated in FIG. 2, the read gradient, $G_x$, is used for this function and is alternated in polarity to produce bipolar, gradient waveforms 215. The frequency of the alternating gradient 215 is set to the same frequency used to drive the MRE transducer, and it typically has a duration of 25 milliseconds. At the same time, the pulse sequence server 118 produces sync pulses as shown at 217, which have the same frequency as and have a specific phase relationship with respect to the alternating gradient pulses 215. These sync pulses 217 are used to produce the drive signals for the magnetic resonance elastography ("MRE") transducer to apply an oscillating stress 219 to the patient. To insure that the resulting waves have time to propagate throughout the field of view, the sync pulses 217 may be turned on well before the pulse sequence begins, as shown in FIG. 2.

The phase of the MR signal 209 is indicative of the movement of the spins. If the spins are stationary, the phase of the MR signal is not altered by the alternating gradient pulses 215, whereas spins moving along the read gradient axis ("$G_x$-axis") will accumulate a phase proportional to their velocity. Spins which move in synchronism and in phase with the alternating magnetic field gradient 215 will accumulate maximum phase of one polarity, and those which move in synchronism, but 180 degrees out of phase with the alternating magnetic field gradient 215 will accumulate maximum phase of the opposite polarity. The phase of the acquired MR signal 209 is thus affected by the "synchronous" movement of spins along the $G_x$-axis.

The pulse sequence in FIG. 2 can be modified to measure synchronous spin movement along the other gradient axes ($G_y$ and $G_z$). For example, the alternating magnetic field gradient pulses may be applied along the phase encoding axis ("$G_y$-axis") as indicated by dashed lines 221, or they may be applied along the slice select axis ("$G_z$-axis") as indicated by dashed lines 222. Indeed, they may be applied simultaneously to two or three of the gradient field directions to "read" synchronous spin movements along any desired direction.

MRE may be implemented using most types of MR imaging pulse sequences. Gradient echo sequences can be readily modified to incorporate the alternating gradient as illustrated in the above-described embodiment. In some cases, however, the characteristics of a gradient echo sequence may not be ideal for a particular application of the technique. For example, some tissues (such as those with many interfaces between materials with dissimilar magnetic susceptibilities) may have a relatively short $T_2^*$ relaxation time and, therefore, may not provide enough signal to obtain a noise-free image at the required echo delay time. In this setting, a spin echo implementation of the invention may be ideal, because for a given echo delay time ("TE"), this pulse sequence is much less sensitive to susceptibility effects than a gradient echo sequence. When a spin echo pulse sequence is used, the alternating magnetic field gradient can be applied either before and/or after the 180 degree RF inversion pulse. However, if the alternating gradient is applied both before and after the RF inversion pulse, the phase of the alternating magnetic field gradient must be inverted 180 degrees after the RF inversion pulse in order to properly accumulate phase.

The material properties of tissue are measured using MRE by applying a stress and observing the resulting strain. For example a tension, pressure, or shear is applied to a subject and the resulting elongation, compression, or rotation is observed. By measuring the resulting strain, material properties of the tissue such as Young's modulus, Poisson's ratio, shear modulus, and bulk modulus can be calculated. Moreover, by applying the stress in all three dimensions and measuring the resulting strain, the material properties of the tissue can be completely defined.

Existing MRE-based methods for calculating the material properties of a tissue employ the application of a so-called "inversion method" to the wave images obtained during an MRE examination. Conventionally, inversion methods describe the propagation of waves in tissues as waves propagating in an infinite medium. This treatment results in inaccuracies for tissue types included the heart, eye, bladder, and prostate, which are more accurately described as a finite, bounded media. As will be discussed below in detail, by employing an inversion method that accounts for the finite nature of certain tissue types, more accurate measurements of tissue material properties are attainable.

By way of example, an inversion method for a thin spherical shell is described herein. The thin spherical shell geometry is applicable to tissues including the heart, the eye, the bladder, and the prostate. The vibrations of a spherical shell include both membrane and flexural effects that result in wave propagation, guided by the boundaries of the object. Expressed in the spherical polar coordinate system, an exemplary thin spherical shell model that assumes midsurface deflections and non-torsional axisymmetric motions is obtained by solving energy balance equation using Hamilton's variational principle both in circumferential and radial direction and is described, for example, by Eqns. (1) and (4), respectively, as follows:

$$(1+\beta^2)\left(\frac{\partial^2 u}{\partial \theta^2} + \cot\theta \frac{\partial u}{\partial \theta} - u(v + \cot^2\theta)\right) - \beta^2 \frac{\partial^3 w}{\partial \theta^3} -$$

$$\beta^2 \cot\theta \frac{\partial^2 w}{\partial \theta^2} + ((1+v) + \beta^2(v + \cot^2\theta))\frac{\partial w}{\partial \theta} - \frac{a^2 \ddot{u}}{c_p^2} = 0;$$

Eqn. (1)

where a is the radius of the shell, u is a circumferential component of the displacement induced by a vibratory motion applied to the subject, w is a radial component of the same displacement; $c_p$ is a flexural wave speed, $\ddot{u}$ is the second derivative with respect to time of the circumferential component of the displacement, u (that is, a circumferential component of acceleration), and β is a parameter having the form:

$$\beta = \frac{h^2}{12a^2};$$

Eqn. (2)

where h is the thickness of the shell. Additionally, the flexural wave speed, $c_p$, has the form:

$$c_p = \frac{E}{(1-v^2)\rho}; \qquad \text{Eqn. (3)}$$

where E is Young's modulus, ν is Poisson's ratio, and ρ is density. In addition to Eqn. (1), which describes flexural waves propagating through the spherical shell, the following flexural wave equation is also supplied:

$$\beta^2 \frac{\partial^3 u}{\partial \theta^3} + 2\beta^2 \cot\theta \frac{\partial^2 u}{\partial \theta^2} - ((1+v)(1+\beta^2) + \beta^2 \cot^2\theta) \frac{\partial u}{\partial \theta} + \qquad \text{Eqn. (4)}$$
$$\beta^2 \cot\theta(2-v+\cot^2\theta) - u(1+v) - \beta^2 \frac{\partial^4 w}{\partial \theta^4} - 2\beta^2 \cot\theta \frac{\partial^3 w}{\partial \theta^3} +$$
$$\beta^2(1+v+\cot^2\theta) \frac{\partial^2 w}{\partial \theta^2} - \beta^2 \cot\theta(2-v+\cot^2\theta) \frac{\partial w}{\partial \theta} -$$
$$2w(1+v) - \frac{a^2 \ddot{w}}{c_p^2} = -p_a \frac{(1-v^2)a^2}{Eh};$$

where $\ddot{w}$ is the second derivative with respect to time of the radial component of the displacement, w (that is, a radial component of the acceleration), and $p_a$ is an applied load. Eqn. (4) describes the propagation of flexural waves, in which the wavelength is greater than the thickness of the shell.

The circumferential and radial displacements are calculated from the in-plane Cartesian components of the motion vector measured using MRE and are used in Eqn. (1) to solve for $c_p$ and in Eqn. (4) to solve for E. In general, Eqn. (4) is solved for E by writing $c_p$ in terms of E using Eqn. (3) above. Once E is known, μ can be obtained through the following relationship:

$$\mu = \frac{E}{2(1+v)}. \qquad \text{Eqn. (5)}$$

Additionally, after determining $c_p$ the shear modulus, μ, can be determined using the following relationship:

$$\mu = \frac{1}{2}(1-v)\rho c_p^2. \qquad \text{Eqn. (6)}$$

Geometries other than a thin spherical shell can be modeled. For example, the appropriate wave equation model for waves propagating in a finite beam is as follows:

$$EI\left(\frac{\partial^4 w}{\partial x^4}\right) = -\rho S \ddot{w}; \qquad \text{Eqn. (7)}$$

where S is the cross sectional area of the beam, w is an axial component of the displacement, and I is the moment of inertia of the beam. The wave equation model in Eqn. (7) is applicable, for example, when performing MRE of bone and in nonmedical applications such as nondestructive testing of materials. Yet another wave equation model that can be utilized when practicing the present invention is that of a thin elastic plate, as follows:

$$D\left(\frac{\partial^4 w}{\partial x^4} + 2\frac{\partial^4 w}{\partial x^2 \partial y^2} + \frac{\partial^4 w}{\partial y^4}\right) = -\rho h \ddot{w}; \qquad \text{Eqn. (8)}$$

where h is the thickness of the plate and D is a parameter having the form:

$$D = \frac{Eh^3}{12(1-v^2)}. \qquad \text{Eqn. (9)}$$

Similar to the model described by Eqn. (7), the wave equation model of Eqn. (8) is applicable, for example, when performing MRE for the nondestructive testing of materials.

The foregoing wave equations that model the propagation of waves in different finite media are solved using an appropriate numerical technique. In general, an inversion method utilizing one of these models requires the evaluation of a plurality of high-order derivatives of the measured displacement field in order to solve for the material properties of interest. In order to reduce the computational burden of such calculations, the wave images produced from the acquired image data are first filtered. Exemplary filtering resulting in the estimation of the high-order derivatives, and is carried out using, for example, a Savitzky-Golay or polynomial filter that is fit to the data in adaptive windows that conform to the boundary of the object of interest (e.g., the tissue under examination). For example, window sizes that are greater than or equal to two-thirds of the apparent wave length of the displacement waves in the waves images are fit to a $2^{nd}$ or $3^{rd}$ order polynomial filter. These filters are desirable because they are relatively insensitive to noise in the wave images and displacement data determined therefrom. The calculation of high-order derivatives is not trivial in the presence of noise, and this step of filtering the data significantly increases the accuracy of the MRE inversion.

Figure 3:
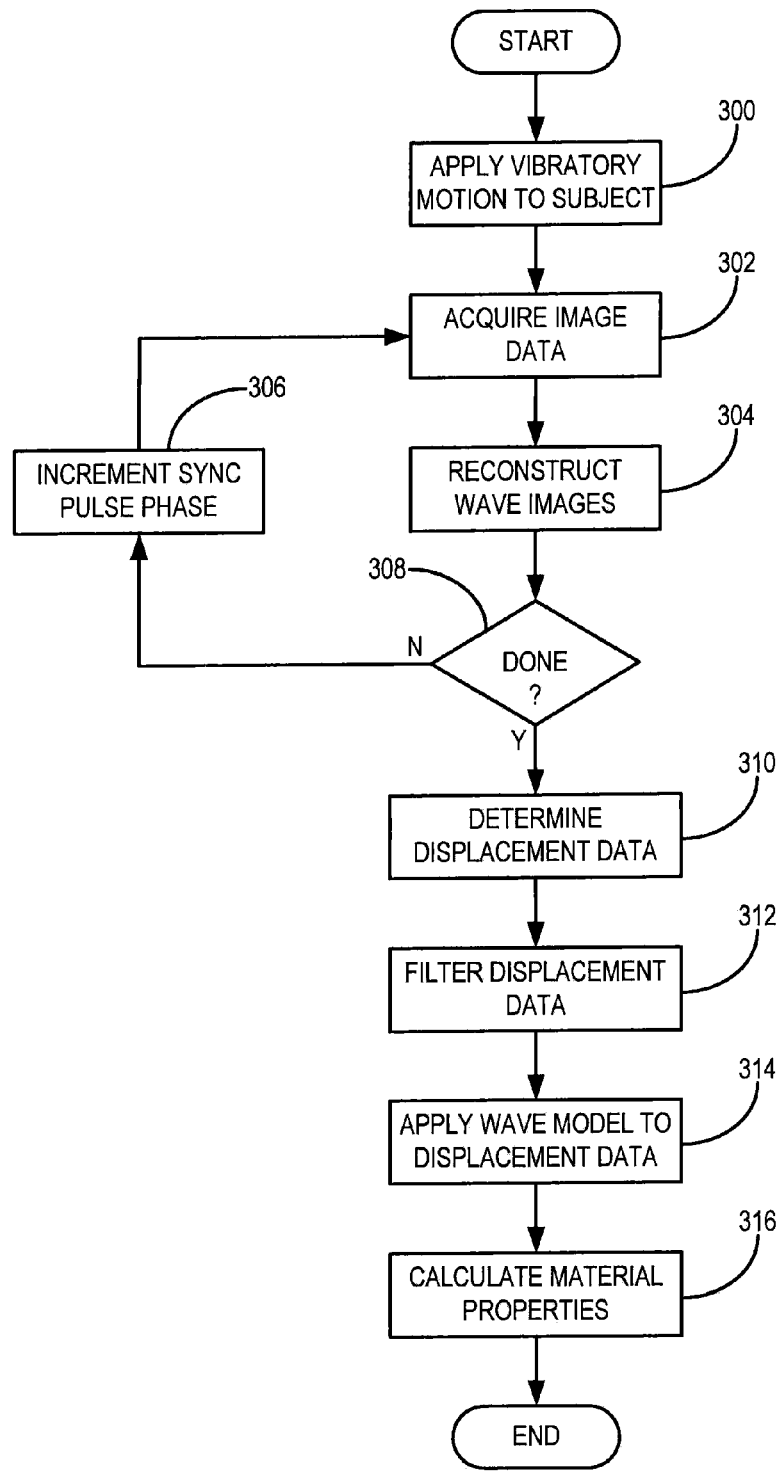
FIG. 3 is a flowchart setting forth the steps of an embodiment of the present invention.

Referring particularly now to FIG. 3, a flowchart setting forth the steps of the method of the present invention begins by applying a vibratory motion to the subject, as indicated at step 300. Image data is subsequently acquired using a pulse sequence suited to perform magnetic resonance elastography ("MRE"), as indicated at step 302. Exemplary pulse sequences include the one described above with reference to FIG. 2. Moreover, exemplary methods for data acquisition during an MRE study are discussed in more detail in U.S. Pat. Nos. 5,592,085 and 5,825,186. Subsequent to the data acquisition, a wave image is reconstructed from the acquired image data, as indicated at process block 304. The intensity of each pixel in this wave image is determined by the phase imparted to spins moving in synchronism with the applied vibratory motion. This synchronous movement is a measure of the strain in the gyromagnetic material and the wave image is, therefore, an image indicative, by the brightness of its pixels, of the strain at corresponding locations in the image plane.

This wave image is a snapshot of the strain at one moment in the applied stress cycle, and to see the strain at other moments, the phase relationship of the sync pulses 217 is changed, as indicated at process block 306, and the acquisition and image reconstruction process is repeated. The scan continues to acquire image data and reconstruct wave images at successive increments of sync pulse phase, for example, increments of 36 degrees. When a desired cycle, for example an entire 360 degree cycle, has been captured in successive wave images the system branches at decision block 308. To this end, a series of wave images indicative of the strain produced by the vibratory motion applied to the subject are produced.

These wave images are also indicative of displacements resulting from waves propagating through the subject. As a result, the set of wave images are subsequently processed to determine displacement data, as indicated at process block 310. Exemplary displacement data includes a displacement vector for each location in the image plane. For example, the displacement data includes a displacement vector indicative of displacement along both the x-axis and the y-axis for each location in the image plane. This displacement data can accordingly transformed into different coordinate systems for analyses in media having different geometries. For example, and as will be described below, the displacement data can be transformed into polar coordinates when determining the material properties in a thin spherical shell.

After the displacement data is determined, it is filtered, as indicated at step 312. For example, and as described above, the displacement data is filtered using a Savitzky-Golay or polynomial filter to estimate the high-order derivatives present in the wave equation model. This step significantly increases the computation efficiency of the MRE inversion method. After the displacement data is filtered in this manner, it is processed using a model of the wave propagation related to the finite medium under examination, as indicated at step 314. Exemplary models of wave propagation are presented in Eqns. (1), (4), (7), and (8) above. By applying the appropriate model to the filtered displacement data, the material properties for the subject are determined, as indicated at step 316. As described above, the application of the model to the displacement data provides an equation or system of equations that, when solved, determine parameters such as the flexural wave speed, $c_p$, and Young's modulus, E. From these parameters, further material properties can be determined, such as the shear stiffness, $\mu$.

Figure 4:
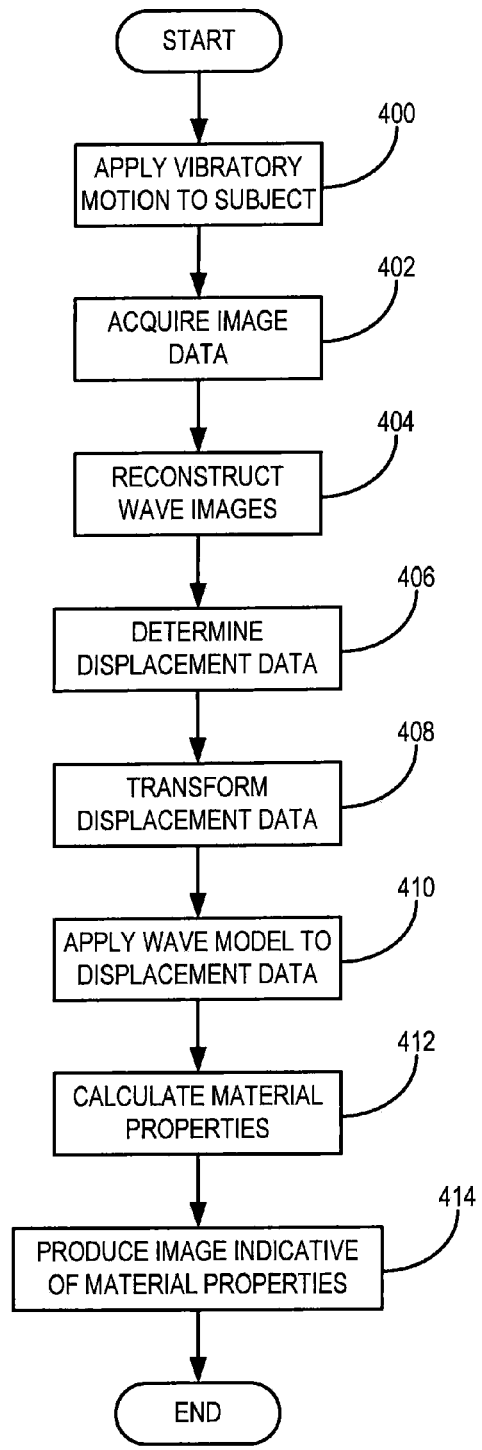
FIG. 4 is a flowchart setting forth the steps of the embodiment of FIG. 3 when employed to determine material properties in a thin spherical shell.

By way of example, the aforementioned method can be employed to produce an image indicative of the material properties of tissues such as the heart, eye, bladder, and prostate. Referring particularly now to FIG. 4, such MRE examinations begin by applying a vibratory motion to the subject, as indicated at step 400. When the MRE examination is that of a subject's heart, an MRE driver such as a pneumatic driver placed on the chest wall is employed to produce shear waves in the subject. Exemplary MRE drivers of this kind are described, for example, in copending U.S. patent application Ser. No. 12/418,204, which is incorporated herein by reference. When the MRE examination is that of a subject's eye, a nylon rod affixed to a piezoelectric disc can be employed to impart vibratory motion to the subject. With such a system, the tip of the nylon rod is placed in contact with the subject's eye, for example, at the sclera. In general, any number of different MRE drivers can be employed to impart vibratory motion to the subject undergoing examination, with each choice of driver depending on the particular clinical application at hand.

As the vibratory motion is being applied to the subject, image data is acquired, as indicated at step 402 and described above in detail. Following the data acquisition, wave images are produced, as indicated as step 404. These wave images are indicative of the waves propagating through the subject and the corresponding displacement field produced thereby. Accordingly, data associated with this displacement field is determined next, as indicated at step 406. As described above in detail, the displacement data includes information related to a displacement vector field in the image plane. From this vector field, individual components of the displacement along a given direction are calculated. When the particular tissue under examination is better described by non-Cartesian coordinates, an appropriate coordinate transformation is applied to the displacement data, as indicated at step 408.

After the displacement data has been determined, the data is fit to the appropriate model of wave propagation, as indicated at step 410. In doing so, the calculation of a plurality of high-order derivatives is performed. To increase the computational efficiency of this calculation, the derivatives are estimated using, for example, a Savitzky-Golay or polynomial filter that is fit to the data in adaptive windows that conform to the boundary of the object of interest. By applying the appropriate model to the displacement data, the material properties for the subject are determined, as indicated at step 412. As described above, the application of the model to the displacement data provides an equation or system of equations that, when solved, determine parameters such as the flexural wave speed, $c_p$, and Young's modulus, E. From these parameters, further material properties can be determined, such as the shear stiffness, $\mu$. When determining the material properties of a tissue of interest using a thin spherical shell model, two calculations are carried out to yield more accurate results. Namely, the model is applied a first time and then rotated 180 degrees and applied again. This allows for accurate calculations at both poles of the spherical shell. After the material properties are calculated in this manner, a corresponding image indicative of said properties is produced, as indicated at step 414.

The present invention has been described in terms of one or more preferred embodiments, and it should be appreciated that many equivalents, alternatives, variations, and modifications, aside from those expressly stated, are possible and within the scope of the invention. For example, while the present invention has been described with respect to particular clinical applications, it can also be employed when practicing MRE in nonclinical applications, such as nondestructive testing.

The invention claimed is:

1. A method for producing an image indicative of an material property in a subject with a magnetic resonance imaging (MRI) system, the steps comprising:
    a) applying a vibratory motion to the subject;
    b) acquiring, with the MRI system, image data from the subject while the vibratory motion is applied;
    c) reconstructing, with a computer, from the acquired image data, a wave image indicative of a displacement in the subject resulting from the applied vibratory motion;
    d) filtering, with the computer, the reconstructed wave image;
    e) providing, with the computer, a model of wave propagation in a finite medium that includes wave equations based on a geometry of a finite medium; and
    f) producing, with the computer, an image indicative of a material property in the subject using the filtered wave image and the provided model of wave propagation in a finite medium.

2. The method as recited in claim 1 in which the finite medium is at least one of a thin spherical shell, a beam, a rod, and a thin plate.

3. The method as recited in claim 1 in which step d) further includes filtering the reconstructed wave image to estimate a derivative included in a wave equation in the model of wave propagation in a finite medium provided in step e).

4. The method as recited in claim 3 in which the derivative is a high-order derivative and filtering is performed using at least one of a Savitzky-Golay filter and a polynomial filter.

5. The method as recited in claim 1 in which the model accounts for waves propagating as a result of at least one of membrane and flexural effects in the finite medium.

6. The method as recited in claim 1 in which producing an image indicative of a material property in the subject in step f) includes calculating a displacement field for each pixel location in the wave image from the filtered wave image.

7. The method as recited in claim 6 in which producing an image indicative of a material property in the subject in step f) includes determining a plurality of displacement vectors from the displacement field.

8. The method as recited in claim 7 in which producing an image indicative of a material property in the subject in step f) further includes applying the model of wave propagation to the determined plurality of displacement vectors.

9. The method as recited in claim 1 in which step d) further includes identifying a region of interest in the wave image.

10. The method as recited in claim 9 in which the reconstructed wave image is filtered in step d) by only filtering pixels in the wave image that are included in the identified region of interest.

11. The method as recited in claim 10 in which the image indicative of a material property in the subject is produced in step f) by applying the model of wave propagation only to the filtered pixels included in the identified region of interest.

* * * * *